US012389930B2

United States Patent
Chen et al.

(10) Patent No.: US 12,389,930 B2
(45) Date of Patent: Aug. 19, 2025

(54) **BREAST MILK-DERIVED *LACTOBACILLUS PLANTARUM* AND USE THEREOF**

(71) Applicant: Beijing Sanyuan Foods Co., Ltd., Beijing (CN)

(72) Inventors: Lijun Chen, Beijing (CN); Lu Liu, Beijing (CN); Chunmei Yin, Beijing (CN); Bin Liu, Beijing (CN); Weiming Zhou, Beijing (CN)

(73) Assignee: BEIJING SANYUAN FOODS CO., LTD., Beijing (CN)

( * ) Notice: Subject to any disclaimer, the term of this patent is extended or adjusted under 35 U.S.C. 154(b) by 545 days.

(21) Appl. No.: 17/788,549

(22) PCT Filed: Jun. 12, 2020

(86) PCT No.: PCT/CN2020/095771
§ 371 (c)(1),
(2) Date: Jun. 23, 2022

(87) PCT Pub. No.: WO2021/248440
PCT Pub. Date: Dec. 16, 2021

(65) Prior Publication Data
US 2023/0050528 A1    Feb. 16, 2023

(51) Int. Cl.
| A23L 33/135 | (2016.01) |
| A23C 9/123 | (2006.01) |
| C12N 1/20 | (2006.01) |
| C12R 1/25 | (2006.01) |

(52) U.S. Cl.
CPC .......... *A23L 33/135* (2016.08); *A23C 9/1234* (2013.01); *C12N 1/205* (2021.05); *A23V 2002/00* (2013.01); *A23V 2400/169* (2023.08); *C12R 2001/25* (2021.05)

(58) Field of Classification Search
None
See application file for complete search history.

(56) References Cited

FOREIGN PATENT DOCUMENTS

| CN | 105505813 | * 12/2015 | ............. C12N 1/205 |
| CN | 105494629 A | 4/2016 | |
| CN | 105505813 A | 4/2016 | |
| KR | 20160012569 A | 2/2016 | |

OTHER PUBLICATIONS

Meiling Jiang et al. Journal of Dairy Sci, vol. 99, pp. 1736-1746, 2015. (Year: 2015).*
International Search Report issued in International Application No. PCT/CN2020/095771; mailed Mar. 9, 2021; 8 pgs.
China General Microbiological Culture Collection Center (CGMCC) situated at Institute of Microbiology, Chinese Academy of Sciences, No. 3, 1# Courtyard, Beichen West Road, Chaoyang District, Beijing, China, with the accession No. CGMCC No. 19748, Apr. 27, 2020; 2 pgs.
Chunmei Vin et al., "Screening and identification of ability lactic acid bacteria from human breast milk and preliminary determination of its ability to hypotensive", Food Science and Technology, 2019, vol. 44, No. 8, p. 18-22; 5 pgs.
Extended European Search Report in Corresponding European Application No. 20940225.4, dated Dec. 9, 2022; 12 pgs.
Notice of Reasons for Refusal in Corresponding Japanese Application No. 2022-519786, dated Nov. 15, 2022; 12 pgs.
Reshma B Nambiar et al., "Characterization of an exopolysaccharide produced by Lactobacillus plantarum HM47 isolated from human breast milk", Process Biochemistry, Elsevier Ltd, GB, vol. 73, Jul. 27, 2018 (Jul. 27, 2018), pp. 15-22; 8 pgs.
Shruti Talashi et al., "Isolation of Lactobacillus plantarum from Human Breast Milk with Probiotic and Medical attributes Former", Acta Scientific Microbiology, Jun. 6, 2019 (Jun. 6, 2019), pp. 163-171; 9 pgs.

* cited by examiner

*Primary Examiner* — Jana A Hines
*Assistant Examiner* — Khatol S Shahnan Shah
(74) *Attorney, Agent, or Firm* — HAUPTMAN HAM, LLP

(57) ABSTRACT

Provided are a breast milk-derived *Lactobacillus plantarum* and use thereof. The breast milk-derived *Lactobacillus plantarum*, which was screened from healthy breast milk, is classified and named as *Lactobacillus plantarum* and has an accession number of CGMCC NO.19748. It has strong adhesion, has an inhibitory effect on 8 commonly known pathogenic bacteria, and is susceptible to 8 antibiotics, and also has strong acid resistance and bile salt resistance.

10 Claims, 5 Drawing Sheets

BREAST MILK-DERIVED *LACTOBACILLUS PLANTARUM* AND USE THEREOF

RELATED APPLICATIONS

The present application is a U.S. National Phase of International Application Number PCT/CN2020/095771 filed Jun. 12, 2020.

TECHNICAL FIELD

The invention relates to the field of microorganisms, and in particular to a breast milk-derived *Lactobacillus plantarum* and use thereof.

BACKGROUND ART

Breast milk, as an essential source of nutrition in the early growth stage of infants, plays a vital role in the growth and development of infants. Numerous studies have confirmed the existence of lactic acid bacteria in breast milk, which has become an important source of lactic acid bacteria and has the potential to explore probiotics. At present, probiotics derived from breast milk are relatively less, including *Lactobacillus gasseri* CECT5714, *Lactobacillus fermentum* CECT5716, *Lactobacillus salivarius* CECT5713, etc., all of which show certain probiotic functions. It is of great significance to continuously explore probiotics from breast milk.

*Lactobacillus plantarum*, as one kind of lactic acid bacteria, is widely contained in meat, milk, vegetables, and fermented products, and has also been found in the digestive tract of human and animals, and is a beneficial bacterium in the human intestine.

The information disclosed in the Background section is only intended to enhance understanding of the general background of the invention and should not be taken as an acknowledgment or implying, in any form, that the information constitutes the prior art already known to those skilled in the art.

SUMMARY OF THE INVENTION

Purpose of Invention

To solve the above technical problems, the invention aims to provide a breast milk-derived *Lactobacillus plantarum* and use thereof. The breast milk-derived *Lactobacillus plantarum* of the invention, which was screened from healthy breast milk, has a very strong adhesion and good probiotic potential. And it shows an inhibitory effect on 8 commonly known pathogenic bacteria with good antibacterial activity, and is susceptible to 8 antibiotics, and thus is expected to be developed and applied in the food industry. In addition, the breast milk-derived *Lactobacillus plantarum* has strong acid resistance and bile salt resistance.

Technical Solutions

To achieve the purpose of the present invention, the present invention provides a breast milk-derived *Lactobacillus plantarum*, which is classified and named as *Lactobacillus plantarum*, and has an accession number of CGMCC NO.19748.

The breast milk-derived *Lactobacillus plantarum* P6 has been deposited in China General Microbiological Culture Collection Center on Apr. 27th, 2020, which is situated at Institute of Microbiology, Chinese Academy of Sciences, No.3, 1# Courtyard, Beichen West Road, Chaoyang District, Beijing, China, with the accession number CGMCC No.19748.

In one possible embodiment of the breast milk-derived *Lactobacillus plantarum*, the adherence rate of the breast milk-derived *Lactobacillus plantarum* to intestinal cells is ≥140%; optionally, the cell is a human colon cancer cell (HT-29).

In one possible embodiment of the breast milk-derived *Lactobacillus plantarum*, the breast milk-derived *Lactobacillus plantarum* has an inhibitory effect on both Gram-positive bacteria and Gram-negative bacteria; optionally, the breast milk-derived *Lactobacillus plantarum* has an inhibitory effect on *Listeria monocytogenes*, *Staphylococcus aureus*, *Bacillus cereus*, *Escherichia coli*, *Shigella sonnei*, *Salmonella typhi*, *Enterobacter sakazakii*, and *Salmonella enteritidis* with the inhibition zone diameter of ≥20 mm; further optionally, the breast milk-derived *Lactobacillus plantarum* has an inhibitory effect on *Escherichia coli* with the inhibition zone diameter of ≥28.5 mm.

In one possible embodiment of the breast milk-derived *Lactobacillus plantarum*, the breast milk-derived *Lactobacillus plantarum* is susceptible to macrolide antibiotics, penicillins, aminoglycosides, lincosamides, cephalosporins, quinolones, and chloramphenicols; optionally, the breast milk-derived *Lactobacillus plantarum* is susceptible to erythromycin, azithromycin, ampicillin, amikacin, clindamycin, ceftriaxone, ciprofloxacin, and chloramphenicol; further optionally, the breast milk-derived *Lactobacillus plantarum* is susceptible to erythromycin, azithromycin, ampicillin, amikacin, clindamycin, ceftriaxone, and ciprofloxacin; and more further optionally, the breast milk-derived *Lactobacillus plantarum* is susceptible to azithromycin, clindamycin, and ceftriaxone.

In one possible embodiment of the breast milk-derived *Lactobacillus plantarum*, the survival rate of the breast milk-derived *Lactobacillus plantarum*, when cultured at pH 2.5 is ≥107% for 3 hours, ≥115% for 6 hours, and ≥74% for 12 hours.

In one possible embodiment of the breast milk-derived *Lactobacillus plantarum*, the survival rate of the breast milk-derived *Lactobacillus plantarum*, when cultured at pH 3.5, is ≥105% for 3 hours, ≥129% for 6 hours, ≥117% for 12 hours, and ≥145% for 24 hours.

In one possible embodiment of the breast milk-derived *Lactobacillus plantarum*, the survival rate of the breast milk-derived *Lactobacillus plantarum*, when cultured at pH 4.5, is ≥132% for 3 hours, ≥174% for 6 hours, ≥107% for 12 hours, and ≥68% for 24 hours.

In one possible embodiment of the breast milk-derived *Lactobacillus plantarum*, the survival rate of the breast milk-derived *Lactobacillus plantarum*, when cultured at pH 3.0, is ≥145% for 1 hour.

In one possible embodiment of the breast milk-derived *Lactobacillus plantarum*, the survival rate of the breast milk-derived *Lactobacillus plantarum*, when cultured in the presence of 0.3% bile salt, is ≥225% for 1 hour.

In one possible embodiment of the breast milk-derived *Lactobacillus plantarum*, the survival rate of the breast milk-derived *Lactobacillus plantarum*, when cultured in the presence of 0.3% bile salt is ≥42% for 3 hours, and ≥19% for 6 hours.

In one possible embodiment of the breast milk-derived *Lactobacillus plantarum*, the survival rate of the breast milk-derived *Lactobacillus plantarum*, when cultured in the presence of 0.15% bile salt is ≥66% for 3 hours, ≥60% for 6 hours, ≥40% for 12 hours, and ≥14% for 24 hours.

The invention also provides a method for preparing the breast milk-derived *Lactobacillus plantarum*, which comprises the following steps:

fresh breast milk samples are selected; after gradient dilution with sterilized PBS, the samples are coated on an MRS medium containing 1% $CaCO_3$, and cultured in an anaerobic incubator at 37° C. for 48 hours; white or milky white well-growing single colonies with obvious transparent circles are selected for Gram staining and microscopic inspection; rod-like strains of Gram-positive bacteria are selected for enrichment culture in an anaerobic incubator at 37° C.; the bacteria solution is mixed with 30% sterilized glycerin in a ratio of 1:1, and then stored in a refrigerator at −80° C. for later use; compared with other kinds of lactic acid bacteria, the probiotic properties of *Lactobacillus* are relatively more advantageous, so the screening target of the invention focuses on *Lactobacillus* among lactic acid bacteria;

the selected strains are tested for acid resistance, bile salt resistance, and adhesion, to obtain a strain of *Lactobacillus plantarum* with the best adhesion as well as good acid resistance and good bile salt resistance.

The invention also provides use of the breast milk-derived *Lactobacillus plantarum* in preparing health food.

In one possible embodiment of the use, the health food includes infant formula food or yogurt.

In one possible embodiment of the use, the health food has health care effects, including enhancing immunity or treating constipation.

Beneficial Effects (1) The breast milk-derived *Lactobacillus plantarum* according to the invention, which was screened from healthy breast milk, has a very strong adhesion (as much as 140%) and good probiotic potential. Adhesion and colonization in the intestinal tract are important premises for lactic acid bacteria to exert their ecological effects and physiological functions, and one of the important indexes for evaluating their probiotic potential. Adherence of lactic acid bacteria to epithelial cells is the main basis for exerting their probiotic functions, the adhered lactic acid bacteria can survive in the intestinal tract and resist the invasion of pathogenic bacteria, and produce metabolites such as antibacterial peptides to help to effectively kill pathogenic bacteria, thus achieving the effects of protecting the intestinal tract from infection of pathogenic bacteria, and enhancing the body's immunity.

(2) Food spoilage is mostly owing to microbial contamination, growth, and reproduction, and the antibacterial activity of probiotics is one of the safety indicators showing whether it can be used in food.

Excessive use of antibiotics in the medical industry will lead to increased drug resistance of pathogenic strains, and disturbance and imbalance of intestinal bacterial flora. Thus antibiotics susceptibility is also one of the important safety indicators showing whether it can be used in food. The breast milk-derived *Lactobacillus plantarum* according to the invention shows an inhibitory effect on 8 commonly known pathogenic bacteria with good antibacterial activity, and exhibits susceptibility to 8 antibiotics, and thus is expected to be developed and applied in the food industry.

(3) The breast milk-derived *Lactobacillus plantarum* according to the invention also has strong acid resistance (the survival rate at pH 3.0 for 1 hour is 145%) and strong bile salt resistance (the survival rate in the presence of 0.3% bile salt for 1 hour is 225%). The premises that lactic acid bacteria can exert their probiotic effect lie in that the lactic acid bacteria can tolerate the acidic condition of human gastric juice (the pH of normal human gastric juice is between 1.5-4.5) and a high level of bile salts in small intestine (the bile salt concentration is 0.03%-0.3%), the bacterial strains can grow and metabolize normally under these conditions, and therefore they can colonize in the gastrointestinal tract and exert their effects.

BRIEF DESCRIPTION OF THE DRAWINGS

One or more examples are exemplified by the pictures in the accompanying drawings that correspond thereto and are not intended to be limiting of the embodiments. As used herein, the word "exemplary" means "serving as an example, embodiment, or illustrative". Any embodiment described herein as "exemplary" is not necessarily to be construed as superior or better than other embodiments.

FIG. 1-2 shows the results of bile salt resistance test recited in Example 1 of the present invention.

FIG. 1-3 shows the results of adhesion test recited in Example 1 of the present invention.

FIG. 2 shows the results of NR database annotation in Example 2 of the present invention.

FIG. 3-1 shows the growth curve of breast milk-derived *Lactobacillus plantarum* P6 as recited in Example 3 of the present invention.

FIG. 3-2 shows the results of acid resistance test in vitro of breast milk-derived *Lactobacillus plantarum* P6 as recited in Example 3 of the present invention.

FIG. 3-3 shows the results of bile salt resistance test in vitro of breast milk-derived *Lactobacillus plantarum* P6 as recited in Example 3 of the present invention.

FIG. 3-4 shows the results of bacteriostatic activity test of breast milk-derived *Lactobacillus plantarum* P6 as recited in Example 3 of the present invention.

Figure 1:
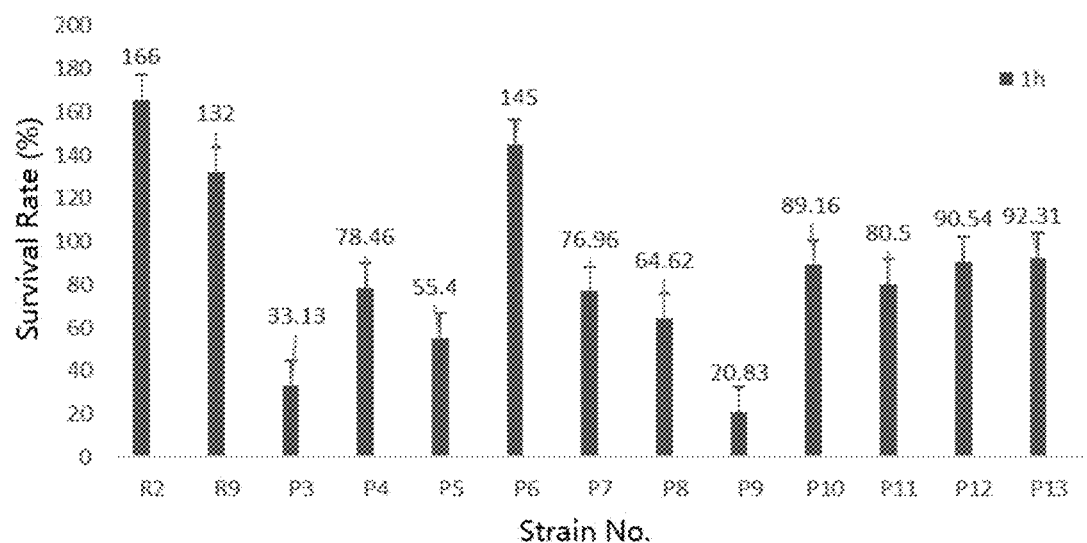
FIG. 1-1 shows the results of acid resistance test recited in Example 1 of the present invention.

The breast milk-derived *Lactobacillus plantarum* P6 provided by the present invention is classified and named as *Lactobacillus plantarum*, has been deposited in China General Microbiological Culture Collection Center on Apr. 27th, 2020, which is situated at Institute of Microbiology, Chinese Academy of Sciences, No.3, 1# Courtyard, Beichen West Road, Chaoyang District, Beijing, China, with the accession number of CGMCC No.19748.

DETAILED DESCRIPTION OF THE INVENTION

In order to make the purpose, technical solutions and advantages of the embodiments of the invention clearer, the technical solutions in the embodiments of the invention will be described clearly and completely, obviously, the described embodiments are some of the embodiments of the present invention, but not all of them. Based on the embodiments of the present invention, all other embodiments obtained by those of ordinary skill in the art without creative work are within the scope of the present invention. Throughout the specification and claims, the term "comprising" or variations thereof, such as "including" or "containing" and the like, will be understood to include the stated components and not to exclude other elements or other components, unless expressly indicated otherwise.

In addition, in order to better explain the present invention, a lot of specific details are given in the following embodiments. It will be understood by those skilled in the art that the present invention may be practiced without certain specific details. In some embodiments, materials, elements, methods, means, etc., well known to those skilled in the art, are not described in detail so as to highlight the spirit of the present invention.

In the following examples,

MRS solid medium was purchased from Beijing Luqiao Technology Co., Ltd. with ITEM NO. CM188;

MRS broth culture medium was purchased from Beijing Luqiao Technology Co., Ltd. with ITEM NO. CM187;

Nutrient agar was purchased from Beijing Luqiao Technology Co., Ltd. with ITEM NO. CM 107;

MH solid medium was purchased from Beijing Luqiao Technology Co., Ltd. with ITEM NO. CM902.

Example 1

1. Isolation of Breast Milk-Derived *Lactobacillus plantarum* P6

Fresh breast milk samples were selected. After gradient dilution with sterilized PBS (purchased from Guangzhou Jet Bio-Filtration Co., Ltd.), the samples were coated on an MRS solid medium containing 1% $CaCO_3$, and cultured in an anaerobic incubator at 37° C. for 48 hours, after which white or milky white single colonies with obvious transparent circles were selected for Gram staining and microscopic inspection, and rod-like strains of Gram-positive bacteria were selected. As such, a well-growing strain P3-P13 was selected from the numerous strains therein for enrichment culture in an anaerobic incubator at 37° C.; the bacteria solution was mixed with 30% sterilized glycerin in a ratio of 1:1, and then stored in a refrigerator at −80V for later use.

2. Strain Screening

The strain P3-P13 preserved with glycerol were inoculated in an MRS broth culture medium under aseptic conditions for anaerobic culture at 37° C. for 24 h and successive activation for three generations; after centrifugation of the bacteria solution, the culture medium was washed with sterilized PBS for 2-3 times;

The strain P3-P13 and control strains R2 and R9 were tested for acid resistance, bile salt resistance, and adhesion.

Among them, R2 and R9 were two strains of breast milk-derived *Lactobacillus plantarum* with superior efficacy that have been previously screened by our company, for which please see the literature in detail: Yin Chunmei, Li Zhen, Jiang Tiemin, et al., Screening and identification of ability lactic acid bacteria from human breast milk and preliminary determination of its ability to hypotensive [J]. Food Science and Technology, 2019(8):18-22.

The procedures for acid resistance, bile salt resistance, and adhesion tests were as follows:

(1) Acid Resistance Test

After washing, the culture medium was suspended in MRS broth medium at pH 3.0 for anaerobic culture at 37° C., and sampled at 0 and 1 hour respectively for gradient dilution, and then coated on MRS solid medium plates for anaerobic culture at 37° C. for 48 hours, followed by counting.

Survival rate (%) of the strain=$N_1/N_0*100$;

in the formula, $N_0$ was the viable count (cfu/mL) at 0 hour; $N_1$ was the viable count (cfu/mL) after tolerance of acid for 1 hour.

The results were shown in FIG. 1-1.

(2) Bile Salt Resistance Test

After washing, the culture medium was suspended in MRS broth medium containing 0.3% bile salt for anaerobic culture at 37° C., and sampled at 0 and 1 hour respectively for gradient dilution, and then coated on MRS solid medium plates for anaerobic culture at 37° C. for 48 hours, followed by counting.

Survival rate (%) of the strain=$N_1/N_0*100$;

in the formula, $N_0$ was the viable count (cfu/mL) at 0 hour; $N_1$ was the viable count (cfu/mL) after tolerance of bile salt for 1 hour.

Figures 1, 2:
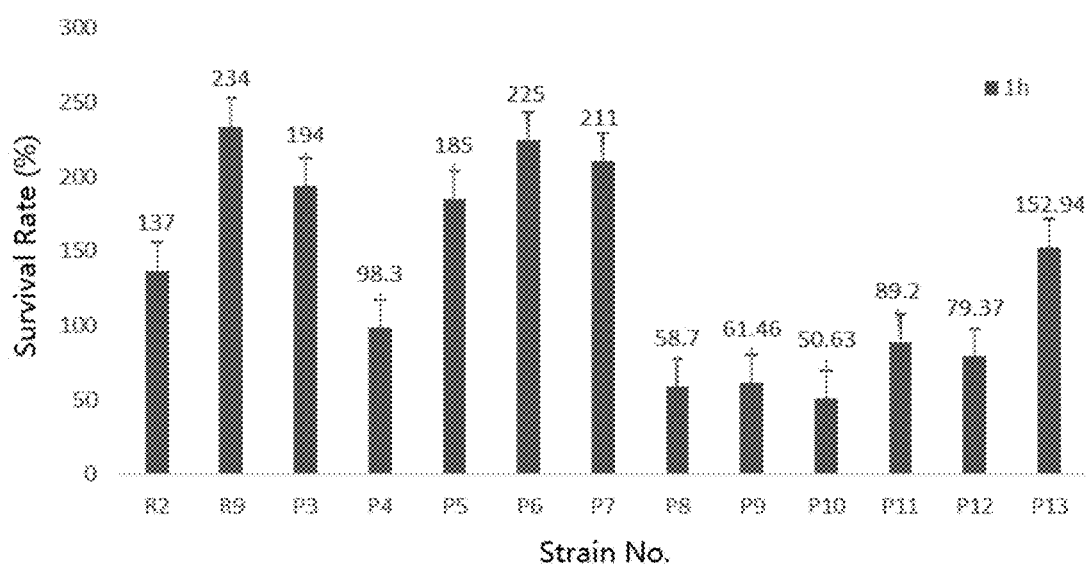

The results were shown in FIG. 1-2.

(3) Adhesion Test

After thawing, HT-29 cells (human colon cancer cells) were inoculated in a cell culture flask in a fresh DMEM complete medium, which was purchased from Thermo Fisher Scientific, and supplemented with 1% penicillin and streptomycin, 1% glutamine, and 10% newborn bovine serum, and incubated in an incubator comprising 5% CO2 at 37° C. The cell culture medium was replaced every two days. As the cells adhered to the wall and grew up to about 70%-80% confluency, 0.25% trypsin-EDTA (purchased from Biological Industries), a mixed digestion solution, was used for subculturing the cells, and DMEM incomplete medium (1% glutamine was added to the DMEM medium) was used as the last medium.

The cultured HT-29 cells were adjusted to a cell concentration of $5\times10^5$ cells/mL using a blood cell counting plate, and loaded into a 6-well tissue culture plate in an amount of 1 mL/well, and incubated in an incubator comprising 5% $CO_2$ at 37° C. until the cells grew into monolayers. the DMEM culture medium in the tissue culture plate was discarded, and the plate was rinsed with sterile PBS for 2-3 times. In the plate, one well was used for cell counting, and the other wells were added with 1 mL of the above prepared bacterial suspension, and incubated for 2 hours in a thermostatic incubator at 37° C. The test was performed for each sample in triplicate. After the incubation, the culture medium was discarded, and the plate was rinsed with sterile PBS buffer for 3-5 times to remove the unattached strains of *Lactobacillus plantarum*. The cells were digested with 0.7 mL of 0.25% trypsin-EDTA until the cells completely fell out. Then 0.3 mL of DMEM complete culture medium was added to stop the digestion, and the culture medium was collected for plate counting.

The adherence rate (%)=the number of adhered bacteria (CFU/well)/the number of HT-29 cells (number/well) *100%;

CFU (colony-forming unit): the total number of bacterial communities per unit volume; in the counting of viable bacteria in culture, the colony formed by the growth and reproduction of single bacteria or multiple bacteria clustered in a solid medium was called colony-forming unit to express the number of viable bacteria.

Figures 1, 2, 3:
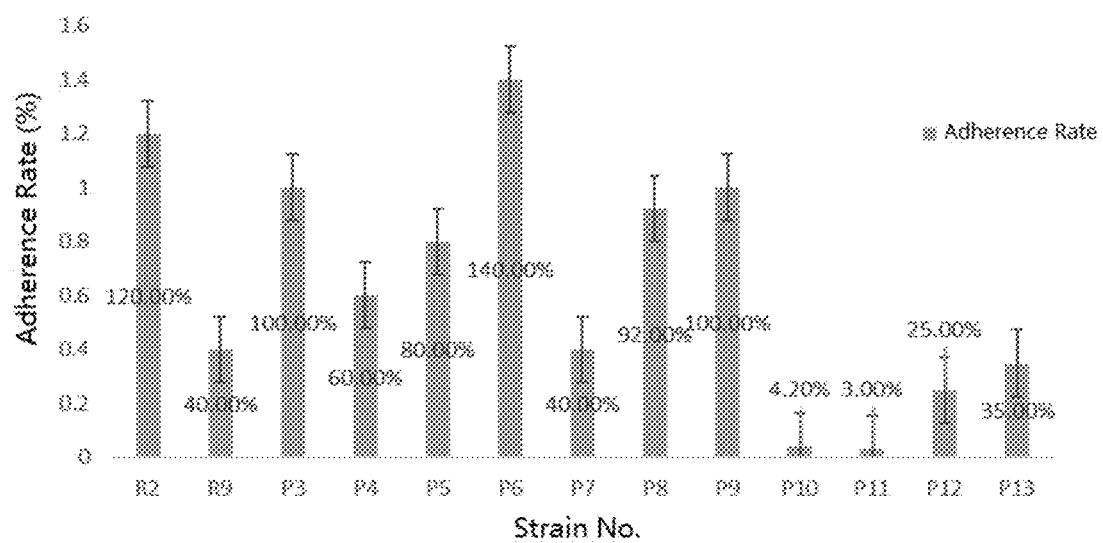
Figure 2:
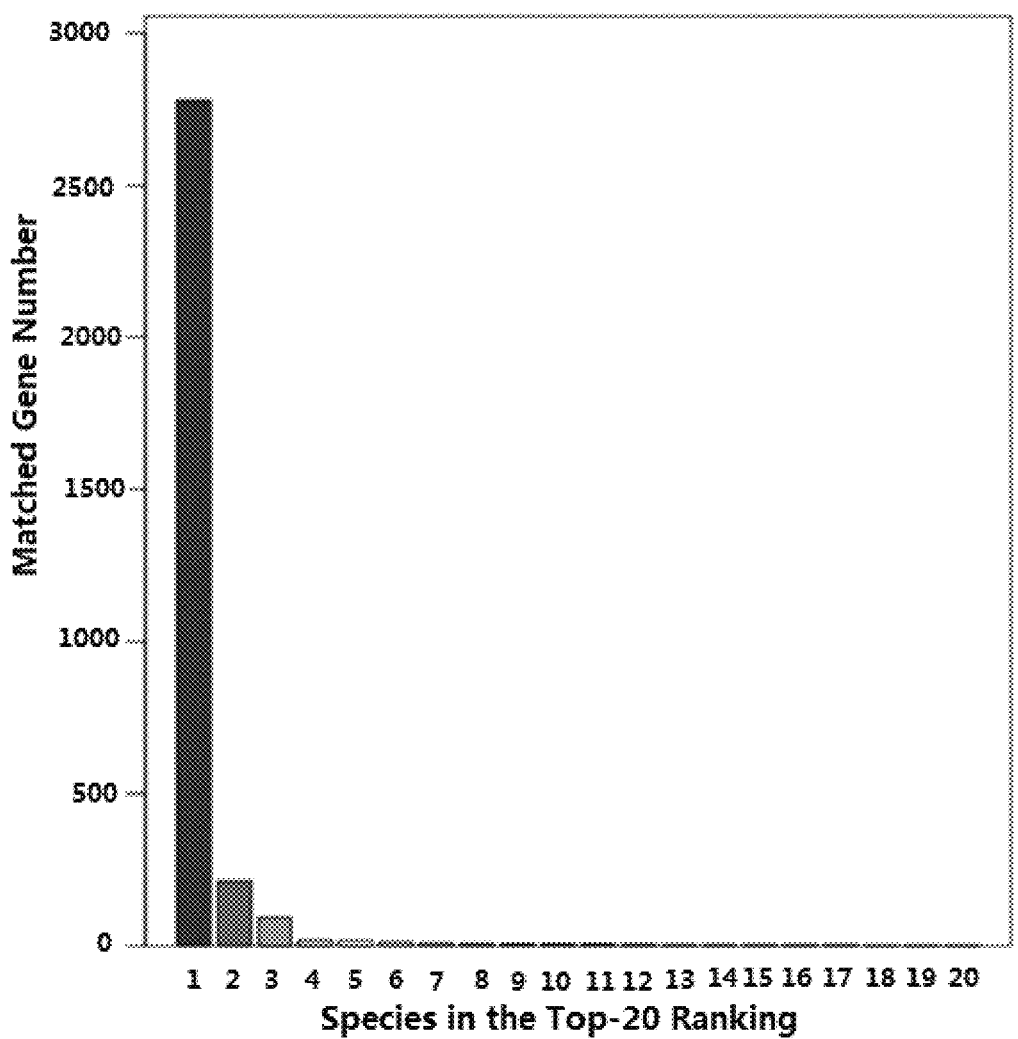

The results were shown in FIG. 1-3.

As can be seen from the results of FIGS. 1-1, 1-2, and 1-3, the adhesion capability of breast milk-derived *Lactobacillus plantarum* P6 was very strong, reaching 140%, which is much higher than that of other breast milk-derived *Lactobacillus plantarum*, and the survival rate thereof is 145% and 225% respectively after 1 hour of culturing under acid and bile salt resistance conditions respectively, showing its good acid resistance and bile salt resistance.

Example 2

Identification of Breast Milk-Derived *Lactobacillus plantarum* P6:

The whole genome sequencing analysis of the breast milk-derived *Lactobacillus plantarum* P6 was performed using Pacbio (10 Kb SMRT Bell library) and Illumina PE150 (350 bp small fragment library) sequencing platforms.

The sequencing results were annotated with NR database (Non-redundant protein database) for identification of species information and classification of species, and the results were shown in FIG. 2.

It can be seen from the results of FIG. 2 that 86.81% of genes conformed to the *Lactobacillus plantarum*, from which, and in combination with the morphological characteristics of the P6, the P6 was identified as *Lactobacillus plantarum*.

Example 3

Determination of Probiotic Properties of Breast Milk-Derived *Lactobacillus plantarum* P6:

1. Determination of Growth Curve of Breast Milk-Derived *Lactobacillus plantarum* P6

The cultured P6 bacteria solution was activated for three generations, and inoculated in an MRS broth culture medium, and then placed in an incubator at 37° C. for anaerobic culture. The viable count of each bacterium was measured at 0, 2, 4, 6, 8, 10, 12, 14, 16, 20, 24, 28, 32, 36, 40, and 48 hours, respectively;

The growth curve of breast milk-derived *Lactobacillus plantarum* P6 was drawn, and the results were shown in FIG. 3-1.

2. Determination of Acid Resistance and Bile Salt Resistance of Breast Milk-Derived *Lactobacillus plantarum* P6 In Vitro The cultured P6 bacteria solution was activated for three generations, inoculated in an MRS broth medium at a pH of 2.5, 3.5, 4.5, and with a bile salt concentration of 0.15%, 0.3%, and 0.45% respectively, and then placed in an incubator at 37° C. for anaerobic culture, and sampled at 0, 3, 6, 12, and 24 hours for plate counting.

The experimental results were shown in FIG. 3-2 and FIG. 3-3, respectively; as can be seen from FIG. 3-2, when the bacterium strain was cultured at pH 6.0, pH 4.5, and pH 3.5 for 0-24 hours, respectively, the growth thereof was stable, and the viable count was more than $10^8$ cfu/mL substantially for all of the treatments, except that it showed a little drop but still exceeded $10^8$ cfu/mL when the bacterium strain was cultured at pH 2.5 for 24 hours; the bacterium strain also showed a strong acid resistance; and the survival data thereof at each time point were shown in Table 1.

TABLE 1

| pH value | 3 h | 6 h | 12 h | 24 h |
|---|---|---|---|---|
| pH 6.0 | 129% | 200% | 120% | 68% |
| pH 4.5 | 132% | 174% | 107% | 68% |
| pH 3.5 | 105% | 129% | 117% | 145% |
| pH 2.5 | 107% | 115% | 74% | 2% |

As can be seen from FIG. 3-3, the growth of the bacterium strain was relatively stable in the medium with a bile salt concentration of 0.15%; and the viable count decreased by 0.71 and 1.6 log values after being cultured for 6 hours in the medium with a bile salt content of 0.3% and 0.45%, respectively; after being cultured at a bile salt concentration of 0.45% for 24 hours, the viable count significantly decreased to $10^5$ cfu/mL; the bacterium strain also showed a strong bile salt resistance; and the survival rate thereof at each time point was shown in Table 2.

TABLE 2

| Bile salt concentration | 3 h | 6 h | 12 h | 24 h |
|---|---|---|---|---|
| 0% | 129% | 200% | 120% | 68% |
| 0.15% | 66% | 60% | 40% | 14% |
| 0.30% | 42% | 19% | 4% | 0% |
| 0.45% | 8% | 3% | 0% | 0% |

3. Determination of Bacteriostatic Activity of Breast Milk-Derived *Lactobacillus plantarum* P6

In daily life, corruption and deterioration occurred often in food which is rich in a lot of nutrients, which endangers human health and causes economic losses. Food spoilage is mostly owing to microbial contamination, growth, and reproduction, and thereby the bacteriostatic ability of the P6 is one of the safety indicators whether it can be used in food.

Eight commonly known foodborne pathogenic bacteria, including *Escherichia coli, Listeria monocytogenes, Staphylococcus aureus, Shigella sonnei, Bacillus cereus, Salmonella typhi, Enterobacter sakazakii*, and *Salmonella enteritidis*, were used as indicator bacteria. After being activated for three generations, the indicator bacteria were coated on nutrient agar, and the antibacterial activity was preliminarily determined by double-layer agar diffusion method.

The Oxford cup (8 mm in diameter) was placed in a plate with tweezers, and the nutrient agar at about 45° C. was poured into the plate to fix the Oxford cup. After solidification of the agar, the Oxford cup was taken out, and 150 μL of the fermentation broth and the supernatant of *Lactobacillus plantarum* P6 were sucked into the well, respectively. Then the plate was put into the refrigerator at 4° C. for diffusion for about 3 hours, and then kept at 37° C. for culture for 24 hours. The inhibition zone diameter was observed and recorded. Each group was tested for three times in parallel, and the results were represented as x±s.

Figures 1, 3:
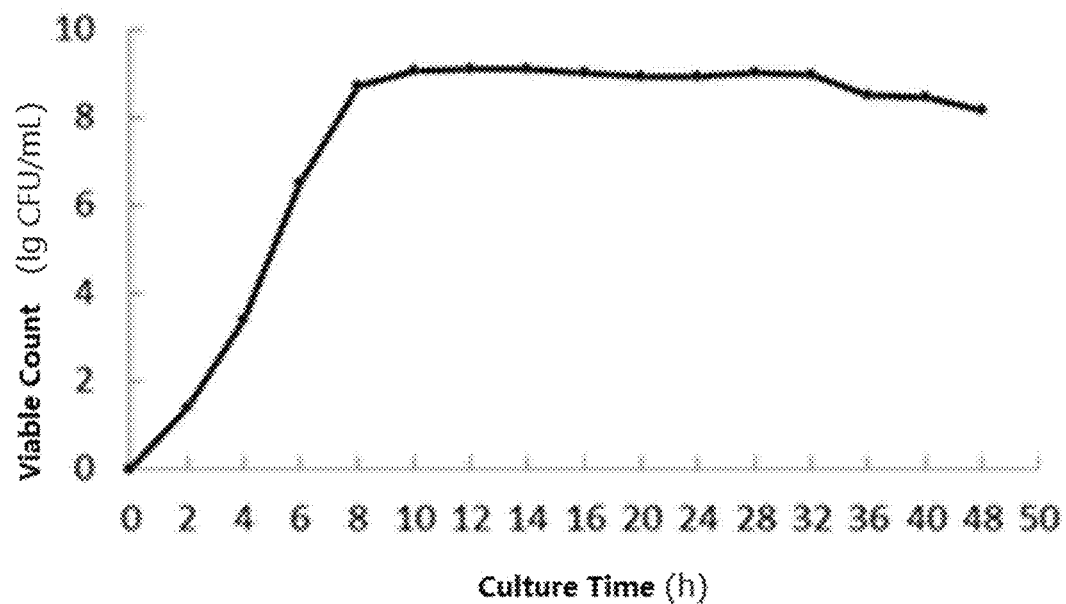
Figures 2, 3:
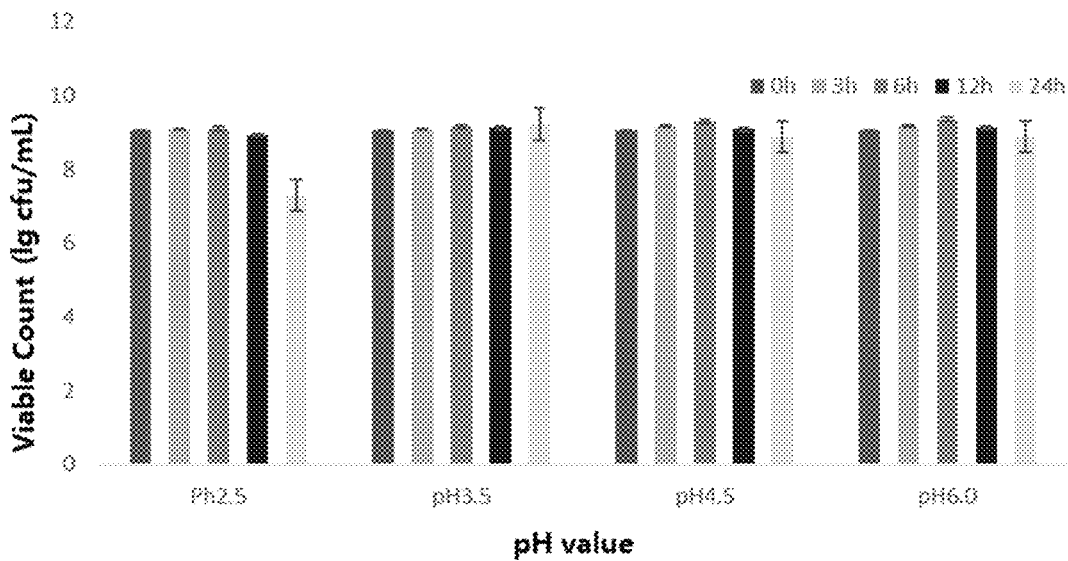
Figure 3:
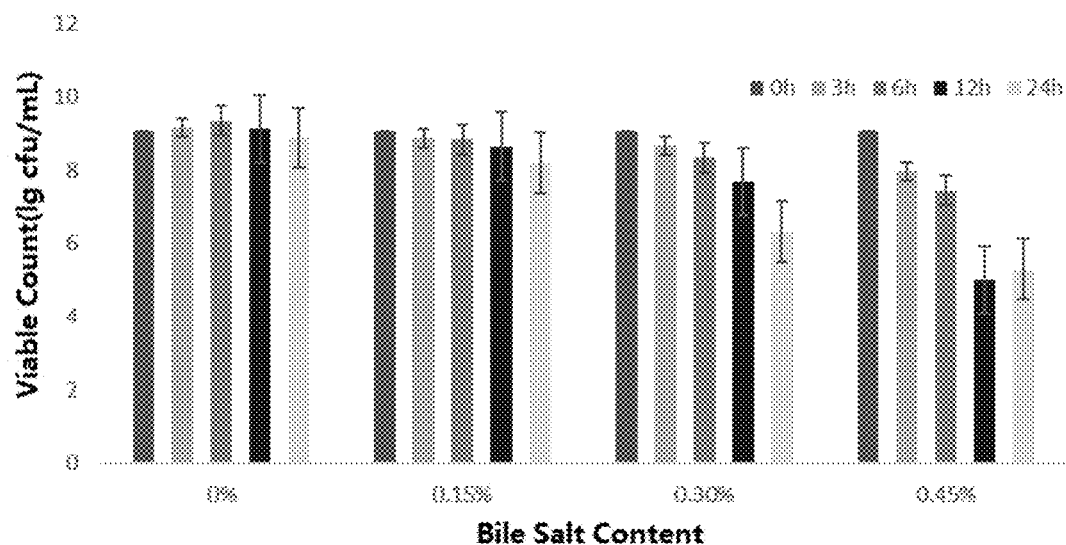
Figures 3, 4:
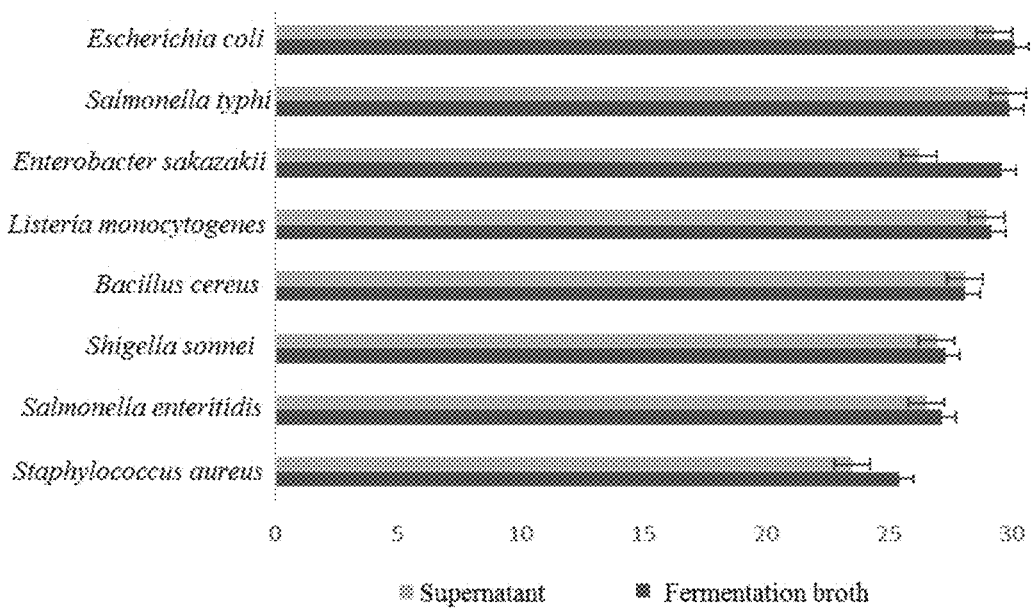

The experimental results were shown in FIG. 3-4. As can be seen from FIG. 3-4, this bacterium had a strong inhibitory effect on both Gram-positive bacteria (*Listeria monocytogenes, Staphylococcus aureus, Bacillus cereus*) and Gram-negative bacteria (*Escherichia coli, Shigella sonnei, Salmonella typhi, Enterobacter sakazakii, Salmonella enteritidis*), and the inhibition zone diameter was all over 20 mm. Among them, the inhibitory effect on *Escherichia coli* was the strongest, and the inhibition zone diameters of the fermentation broth and the supernatant were 30.17±1.58 mm and 29.30±0.72 mm, respectively.

4. Determination of Drug Resistance of Breast Milk-Derived *Lactobacillus plantarum* P6

Excessive use of antibiotics in the medicinal industry will lead to increased drug resistance of pathogenic strains, and disorder and imbalance of intestinal bacterial flora, and thus antibiotic susceptibility is also one of the important safety indicators whether lactic acid bacteria can be used in food.

The cultured P6 bacteria solution was activated for three generations, and streaked on the MRS solid medium plate, which was then cultured in an anaerobic incubator at 37° C. for 24 hours. A single colony was picked up and dissolved in normal saline to prepare a suspension equivalent to 0.5 Maxwell's concentration, which was then coated on an MH solid medium. After drying, ten E-test strips were attached onto the MH solid medium, and cultured at 37° C. for 24-48 hours. The MIC value (minimum inhibitory concentration value) was determined according to the inhibition zone diameter. *Escherichia coli* ATCC25922 and *Staphylococcus aureus* ATCC25923 were used as quality-control strains. Quality-control strains were used as control for each batch test, and the MIC of the quality-control strains was required to be within the range specified by CLSI (Clinical and Laboratory Standards Association). An MH solid plate without antibiotics was used as blank control.

The results were shown in Table 3. As can be seen from Table 3, the *Lactobacillus plantarum* P6 was extremely susceptible to erythromycin and azithromycin (macrolide antibiotics), ampicillin (penicillins), amikacin (aminoglycosides), clindamycin (lincosamides), ceftriaxone (cephalosporins), and ciprofloxacin (quinolones), and intermediately susceptible to chloramphenicol (chloramphenicols), and was resistant to penicillin G (penicillins) and tetracycline (tetracyclines).

TABLE 3

| Categories | Antibiotics | Minimum inhibitory concentration MIC (µg/mL) |
|---|---|---|
| Macrolides | erythromycin | 0.38/S |
|  | Azithromycin | 0.094/S |
| Penicllins | ampicillin | 1.5/S |
| Aminoglycosides | amikacin | 2/S |
| Lincosamidess | clindamycin | 0.016/S |
| Cephalosporins | ceftriaxone | 0.125/S |
| Quinolones | ciprofloxacin | 3/S |
| Chloramphenicols | chloramphenicol | 16/I |
| Penicillins | penicillin G | 32/R |
| Tetracyclines | tetracycline | 256/R |

S: susceptible;
I: intermediate;
R: resistance

To sum up, the breast milk-derived *Lactobacillus plantarum* P6 has good growth characteristics, strong acid and bile salt resistance, and very strong adhesion, and has an inhibitory effect on eight commonly known pathogenic bacteria with good antibacterial activity, and exhibits susceptibility to 8 antibiotics. The above results have indicated that the breast milk-derived *Lactobacillus plantarum* P6 has excellent probiotic potential and is expected to be developed and applied in the food industry.

Finally, it should be noted that the above embodiments are only used to illustrate the technical solutions of the present invention and not to limit it; although the present invention has been described in detail with reference to the foregoing embodiments, it will be understood by one of ordinary skill in the art that the technical solutions described in the foregoing embodiments can still be modified or some technical features can be equivalently substituted; however, these modifications or substitutions do not make the essence of the corresponding technical solutions departing from the spirit and scope of the technical solutions of various embodiments of the present invention.

INDUSTRIAL APPLICABILITY

The invention provides the breast milk-derived *Lactobacillus plantarum* and use thereof. The breast milk-derived *Lactobacillus plantarum*, which was screened from healthy breast milk, is classified and named as *Lactobacillus plantarum* under the accession number of CGMCC NO.19748, and has strong adhesion capability and good probiotic potential. And it shows an inhibitory effect on 8 commonly known pathogenic bacteria with good antibacterial activity, and is susceptible to 8 antibiotics, and thus is expected to be developed and applied in the food industry. In addition, the breast milk-derived *Lactobacillus plantarum* still has strong acid resistance and bile salt resistance.

The invention claimed is:
1. A biologically pure culture of a breast milk-derived *Lactobacillus plantarum*, wherein the breast milk-derived *Lactobacillus plantarum* has an accession number of CGMCC NO.19748.
2. The biologically pure culture according to claim 1, wherein the adherence rate of the breast milk-derived *Lactobacillus plantarum* to intestinal cells is ≥140%.
3. The biologically pure culture according to claim 1, wherein the adherence rate of the breast milk-derived *Lactobacillus plantarum* to human colon cancer cells is ≥140%.
4. The biologically pure culture according to claim 1, wherein the breast milk-derived *Lactobacillus plantarum* has an inhibitory effect on both Gram-positive bacteria and Gram-negative bacteria; optionally, the breast milk-derived *Lactobacillus plantarum* has an inhibitory effect on *Listeria monocytogenes*, *Staphylococcus aureus*, *Bacillus cereus*, *Escherichia coli*, *Shigella sonnei*, *Salmonella typhi*, *Enterobacter sakazakii*, and *Salmonella enteritidis*; further optionally, the breast milk-derived *Lactobacillus plantarum* has an inhibitory effect on *Escherichia coli*.
5. The biologically pure culture according to claim 1, wherein the breast milk-derived *Lactobacillus plantarum* is susceptible to macrolide antibiotics, penicillins, aminoglycosides, lincosamides, cephalosporins, quinolones, and chloramphenicols; optionally, the breast milk-derived *Lactobacillus plantarum* is susceptible to erythromycin, azithromycin, ampicillin, amikacin, clindamycin, ceftriaxone, ciprofloxacin, and chloramphenicol; further optionally, the breast milk-derived *Lactobacillus plantarum* is susceptible to azithromycin, clindamycin, and ceftriaxone.
6. The biologically pure culture according to claim 1, wherein the survival rate of the breast milk-derived *Lactobacillus plantarum*, when cultured at pH 2.5, is ≥107% for 3 hours, ≥115% for 6 hours, and >74% for 12 hours;
and/or, the survival rate of the breast milk-derived *Lactobacillus plantarum*, when cultured at pH 3.5, is ≥105% for 3 hours, ≥129% for 6 hours, ≥117% for 12 hours, and >145% for 24 hours;
and/or, the survival rate of the breast milk-derived *Lactobacillus plantarum*, when cultured at pH 4.5, is ≥132% for 3 hours, ≥174% for 6 hours, ≥107% for 12 hours, and ≥68% for 24 hours;
and/or, the survival rate of the breast milk-derived *Lactobacillus plantarum*, when cultured at pH 3.0, is ≥145% for 1 hour.
7. The biologically pure culture according to claim 1, wherein the survival rate of the breast milk-derived *Lactobacillus plantarum*, when cultured in the presence of 0.3% bile salt, is ≥225% for 1 hour;
and/or, the survival rate of the breast milk-derived *Lactobacillus plantarum*, when cultured in the presence of 0.3% bile salt, is ≥42% for 3 hours, and ≥19% for 6 hours;
and/or, the survival rate of the breast milk-derived *Lactobacillus plantarum*, when cultured in the presence of 0.15% bile salt, is ≥66% for 3 hours, ≥60% for 6 hours, ≥40% for 12 hours, and ≥14% for 24 hours.
8. A health food which comprises the breast milk-derived *Lactobacillus plantarum* recited in claim 1.
9. The health food according to claim 8, wherein the health food comprises infant formula food or yogurt.
10. The health food according to claim 8, wherein the health food has health care effects, including enhancing immunity or treating constipation.

* * * * *